United States Patent
Brehm et al.

(10) Patent No.: US 11,197,818 B2
(45) Date of Patent: Dec. 14, 2021

(54) AQUEOUS EMULSIONS OF CARBAMATO-FUNCTIONALIZED ORGANOPOLYSILOXANES

(71) Applicant: Wacker Chemie AG, Munich (DE)

(72) Inventors: Christof Brehm, Burghausen (DE); Gerhard Beer, Burghausen (DE); Werner Limmer, Pleiskirchen (DE)

(73) Assignee: WACKER CHEMIE AG, Munich (DE)

( * ) Notice: Subject to any disclaimer, the term of this patent is extended or adjusted under 35 U.S.C. 154(b) by 397 days.

(21) Appl. No.: 16/096,184

(22) PCT Filed: Apr. 24, 2017

(86) PCT No.: PCT/EP2017/059644
§ 371 (c)(1),
(2) Date: Oct. 24, 2018

(87) PCT Pub. No.: WO2017/186633
PCT Pub. Date: Nov. 2, 2017

(65) Prior Publication Data
US 2019/0133919 A1    May 9, 2019

(30) Foreign Application Priority Data
Apr. 26, 2016 (DE) ..................... 10 2016 207 060.6

(51) Int. Cl.
| | |
|---|---|
| *A61K 8/898* | (2006.01) |
| *A61K 8/86* | (2006.01) |
| *A61K 8/06* | (2006.01) |
| *A61Q 5/02* | (2006.01) |
| *A61Q 5/12* | (2006.01) |
| *C08G 77/388* | (2006.01) |
| *A61K 8/89* | (2006.01) |

(52) U.S. Cl.
CPC ............. *A61K 8/898* (2013.01); *A61K 8/06* (2013.01); *A61K 8/062* (2013.01); *A61K 8/86* (2013.01); *A61Q 5/02* (2013.01); *A61Q 5/12* (2013.01); *C08G 77/388* (2013.01); *A61K 8/89* (2013.01); *A61K 2800/21* (2013.01)

(58) Field of Classification Search
CPC . A61K 8/89; A61K 8/06; A61K 8/062; A61K 2800/21
See application file for complete search history.

(56) References Cited

U.S. PATENT DOCUMENTS

| | | | |
|---|---|---|---|
| 3,642,858 A | 2/1972 | Frevel et al. | |
| 4,620,878 A | 11/1986 | Gee | |
| 5,389,364 A | 2/1995 | Cifuentes et al. | |
| 6,153,569 A | 11/2000 | Halloran | |
| 2011/0097567 A1 | 4/2011 | Steffanut | |
| 2011/0104085 A1* | 5/2011 | Klug | A61Q 5/004 424/59 |
| 2012/0270985 A1 | 10/2012 | Ando et al. | |

FOREIGN PATENT DOCUMENTS

| | | |
|---|---|---|
| EP | 0639369 A1 | 2/1995 |
| EP | 1972330 A2 | 9/2008 |
| WO | 09150213 A1 | 12/2009 |

OTHER PUBLICATIONS

Ullmann's Encylopedia of Industrial Chemistry, CD-ROM—Ausgabe 2003, Wiley-VCH Verlag.
K. Krummel, Stephane Chiron, J. Jachowicz, Chapter 14, The Chemistry and Manufacture of Cosmetics, vol. II, Formulating, Third Edition, Mitechell L. Schlossmann, 2000, S. 359-396.
International Cosmetic Ingredient Dictionary and Handbook, 13th Edition, The Personal Care Product Council, 2010, http://online.personalcarecouncil.org/jsp/Home.jsp.
K. Schrader, A. Domsch, Cosmetology—Theory and Practice, vol. II, Seite II-8 bis II-22, Verlag für chemische Industrie, 2005, Punkt 1. bis 18.
G. Engelhardt, H. Jancke; J. Oganometal. Chem. 28 (1971), 293-300.
"Chapter 8—NMR spectroscopy of organosilicon compounds", Elizabeth A. Williams, The Chemistry of Organic Silicon Compounds, 1989, John Wiley and Sons Ltd., 511-533.
Y. K. Kamath, Hans-Dietrich Weigmann, J. Soc. Cosmet. Chem., 37, 111-124, 1986.

* cited by examiner

*Primary Examiner* — James W Rogers
(74) *Attorney, Agent, or Firm* — Brooks Kushman P.C.

(57) ABSTRACT

Aqueous nanoemulsions of carbamato-functional organopolysiloxanes prepared using a polyoxyethylene emulsifier having an HLB greater than 15 and at least 40 oxyethylene moieties and having a $D_{50}$ particle size ≤100 nm are transparent, stable, and useful in cosmetic compositions, particularly hair care compositions.

19 Claims, No Drawings

AQUEOUS EMULSIONS OF CARBAMATO-FUNCTIONALIZED ORGANOPOLYSILOXANES

CROSS REFERENCE TO RELATED APPLICATIONS

This application is the U.S. National Phase of PCT Appln. No. PCT/EP2017/059644 filed Apr. 24, 2017, which claims priority to German Application No. 10 2016 207 060.6 filed Apr. 26, 2016, the disclosures of which are incorporated in their entirety by reference herein.

BACKGROUND OF THE INVENTION

1. Field of the Invention

The invention relates to aqueous emulsions of carbamato-functionalized organopolysiloxanes, to the production thereof and to the use thereof in cosmetic compositions.

2. Description of the Related Art

Silicones as a constituent of cosmetic compositions have long been known. The same applies to carbamato-functionalized polydiorganosiloxanes, as described, for example, in EP 639 369 A1. The carbamato-functionalized polydiorganosiloxanes used therein (prepared by reaction of amino-functionalized polydiorganosiloxanes with ethylene carbonate and/or propylene carbonate), for conditioning of hair, are added in substance to the hair conditioner-containing composition. In clear/transparent cosmetic products, the use of unformulated polydiorganosiloxanes is frequently ruled out since the cosmetic compositions frequently turn cloudy and also lose stability as a result. This is to be observed especially in the case of polysiloxanes of high amine value or in the case of polydiorganosiloxanes that are prepared from amino-functionalized polydiorganosiloxanes of relatively high amine value. This is the case in the examples of EP 639 369 A1 (amine value >0.5 mmol/g).

EP 1 972 330 likewise describes the use of carbamato-functionalized polydiorganosiloxanes in substance in cosmetic products, where the carbamato-functionalized polydiorganosiloxanes are prepared by the reaction with glycerol carbonate.

WO 2009/150213 discloses analogous products (prepared by reaction of amino-functionalized polydiorganosiloxanes of relatively high amine value of greater than 0.5 mmol/g and glycerol carbonate) for the finishing of organic fibers and textiles.

One way of incorporating organopolysiloxanes into cosmetic compositions is to provide them in the form of emulsions, especially in the form of microemulsions for clear/transparent cosmetic compositions. Microemulsions are thermodynamically stable mixtures of water (aqueous phase), oil (water-immiscible phase) and surfactant (solubilizer).

Microemulsions in which the oil phases are formed to a crucial degree by polysiloxanes are known.

U.S. Pat. No. 4,620,878 discloses the production of emulsions and microemulsions containing amino-functional polydiorganosiloxanes. In the method described therein, a concentrate consisting of surfactant, polydiorganosiloxane and small amounts of water is first prepared, which is diluted with water to form the microemulsion.

U.S. Pat. No. 6,153,569 describes the use of microemulsions comprising amino-functionalized polydiorganosiloxanes in order to obtain clear shampoo compositions. Amino-functionalized polydiorganosiloxanes of relatively high amine value (>0.16 mmol/g) are used since the production of microemulsions with amino-functionalized polydiorganosiloxanes of relatively low amine value can be achieved only with difficulty.

When the polydiorganosiloxanes have been functionalized by hydrophilic groups, especially with a relatively large number of hydroxyl groups, it is possible to prepare microemulsions. One example is, for example, the microemulsion of the reaction product of amino-functionalized polydiorganosiloxane of amine value 0.98 mmol/g and glycerol carbonate, as described in WO 2009/150213 A1. The crucial factor here is the level of hydroxyl groups relative to the silicone. In the example cited in WO 2009/150213 A1, there are about 3.13% by weight of HO groups.

The problem addressed was that of providing aqueous emulsions of carbamato-functionalized organopolysiloxanes having small particle size, where the organopolysiloxanes have only a low content of hydroxyl groups, and the emulsions are clear and suitable for production of clear cosmetic compositions which, even after storage, have only very small changes in viscosity, if any.

The problem was solved by the invention.

SUMMARY OF THE INVENTION

The invention provides aqueous emulsions comprising
(A) carbamato-functionalized organopolysiloxanes containing an average per molecule of at least one carbamato-functional Y group of the formula

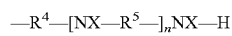

where
X is the same or different and is a hydrogen atom or is a Z radical of the formula

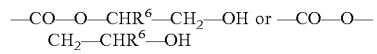

where an average of at least one X radical per molecule is a Z radical,
where $R^4$ is the same or different and is a divalent, Si—C-bonded hydrocarbyl radical having 1 to 18 carbon atoms,
$R^5$ is the same or different and is a divalent hydrocarbyl radical having 1 to 6 carbon atoms,
$R^6$ is the same or different and is a hydrogen atom or a monovalent hydrocarbyl radical having 1 to 36 carbon atoms, where one or more —$CH_2$— groups may be replaced by heteroatoms, preferably by —O— or —S—, and
n is 1, 2, 3 or 4, preferably 1,
(B) nonionic, polyethylene oxide-containing emulsifiers containing more than 40 ethylene oxide units of the formula —$CH_2$—$CH_2$—O—, and having an HLB value of not less than 15, and
(C) water,
where the emulsions have particle sizes of not more than 100 nm (D50).

DETAILED DESCRIPTION OF THE PREFERRED EMBODIMENTS

The emulsions of the invention contain preferably at least 5% by weight, more preferably at least 10% by weight, and preferably at most 50.0% by weight, more preferably at most 35% by weight, most preferably at most 25% by weight, of carbamato-functionalized organopolysiloxanes (A).

The emulsions of the invention contain preferably at least 0.5% by weight, more preferably at least 0.8% by weight, most preferably at least 1.2% by weight, and preferably at most 20% by weight, more preferably at most 15% by weight, and most preferably at most 10% by weight, of nonionic, polyethylene oxide-containing emulsifiers (B).

The emulsions of the invention preferably contain at least 1% by weight, more preferably at least 5% by weight, especially at least 10% by weight, and preferably at most 94.5% by weight, more preferably at most 85% by weight, especially at most 80% by weight, of water (C).

The emulsions of the invention preferably have particle sizes (D50) of not more than 80 nm, more preferably not more than 50 nm, and most preferably not more than 40 nm.

The aqueous emulsions of the invention may optionally, in addition to the
(A) carbamato-functionalized organopolysiloxanes,
(B) nonionic, polyethylene oxide-containing emulsifiers containing more than 40 polyethylene oxide units of the formula —$CH_2$—$CH_2$—O—, and having an HLB value of not less than 15,
and
(C) water,
comprise further ingredients such as
(D) further ionic or nonionic emulsifiers or mixtures thereof having an HLB value of less than 15 in each case,
(E) nonaqueous solvents or coemulsifiers and
(F) auxiliaries such as pH regulators, salts, foam inhibitors, thickeners and/or protective colloids, preservatives, disinfectants, wetting agents, corrosion inhibitors, dyes, fragrances or mixtures thereof.

Carbamato-functionalized polydiorganosiloxanes (A) have long been known and are described, for example, in JP 2047371 A2.

In the compositions of the invention, preference is given to using carbamato-functionalized organopolysiloxanes (A) containing the following structural units:
M [$R^1_2R^2SiO_{1/2}$] and/or M' [$R^1_2(Y)SiO_{1/2}$]
and
D [$R^1_2SiO_{2/2}$] and/or D' [$R^2(Y)SiO_{2/2}$] and/or T' [(Y)$SiO_{3/2}$] and optionally
T [$R^1SiO_{3/2}$] and/or
Q [$SiO_{4/2}$],
with the proviso that on average per molecule, at least one structural unit having a carbamato-functional group Y is present, and where on average per molecule at least one Y group contains a Z radical,
where
$R^1$ is the same or different and is a monovalent Si—C-bonded hydrocarbyl radical having 1 to 18 carbon atoms,
$R^2$ is the same or different and is an $R^1$ radical or a hydroxyl group —OH or alkoxy group of the formula —O—$R^3$ where $R^3$ is an optionally substituted alkyl radical having 1-8 carbon atoms, and Y is as defined above.

In the compositions of the invention, preference is given to using carbamato-functionalized polydiorganosiloxanes (A) of the following formula:

$$[R^1_2R^2SiO_{1/2}]_2[R^2(Y)SiO_{2/2}]_k[R^1_2SiO_{2/2}]_m \tag{I}$$

where
$R^1$, $R^2$ and Y are as defined above,
where on average per molecule at least one Y group contains a Z radical,
m is an integer and is at least 40, preferably at least 65, more preferably at least 110, and at most 1000, preferably at most 800, more preferably at most 500, k is an integer and is at least 1, preferably at least 2, and at most 15, preferably at most 10, more preferably at most 7, where the ratio of m to k is at least 65, preferably at least 100, more preferably at least 130, and at most 1000, preferably at most 800, more preferably at most 600.

It is optionally also possible for small amounts of structural units T or Q to be present in the carbamato-functionalized polydiorganosiloxanes (A) of the formula (I).

In the carbamato-functionalized organopolysiloxanes (A), especially carbamato-functionalized polydiorganosiloxanes (A), preferably at least 5 mol %, more preferably at least 15 mol %, most preferably at least 20 mol %, and preferably less than 100 mol %, more preferably less than 75 mol %, most preferably less than 50 mol %, of the N-bonded X radicals in the Y groups are not a hydrogen atom, but have the meaning of the Z radical.

This means that preferably at least 5 mol % and preferably less than 100 mol %, more preferably less than 50 mol %, of the amino groups have been functionalized by Z radicals, i.e. carbamato groups.

It is possible to use one kind of carbamato-functionalized organopolysiloxanes (A) of the invention or mixtures of two or more kinds.

The carbamato-functionalized organopolysiloxanes (A) used in the compositions in accordance with the invention are preferably prepared by reaction of amino-functionalized organopolysiloxanes (A') containing on average per molecule at least one group Y' of the formula —$R^4$—[NH—$R^5$—]$_n$$NH_2$ where $R^4$, $R^5$ and n are as defined above, with cyclic carbonates.

For preparation of the carbamato-functionalized organopolysiloxanes (A), preference is given to using amino-functionalized polydiorganosiloxanes (A') of the following formula:

$$[R^1_2R^2SiO_{1/2}]_2[R^2(Y')SiO_{2/2}]_k[R^1_2SiO_{2/2}]_m \tag{I'}$$

where
$R^1$, $R^2$, m, and k are as defined above,
Y' is a group of the general formula —$R^4$—[NH—$R^5$—]$_n$$NH_2$ where $R^4$, $R^5$ and n are as defined above.

Cyclic carbonates used are preferably those of the following formula:

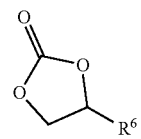

where
$R^6$ is as defined above.

For preparation of the carbamato-functionalized organopolysiloxanes (A), the amount of cyclic carbonate used is selected such that, in the carbamato-functionalized organopolysiloxane (A) prepared, preferably at least 5 mol %, more preferably at least 15 mol %, most preferably at least 20 mol %, and preferably less than 100 mol %, more preferably less than 75 mold, most preferably less than 50 mol %, of the N-bonded X radicals in the Y groups are converted to Z radicals.

The reaction of amino-functionalized organopolysiloxanes (A') with carbamato-functionalized organopolysiloxanes (A) obtained from cyclic carbonates generates hydroxyl groups. The amount of hydroxyl groups (% by weight of OH) in the carbamato-functionalized organopolysiloxanes (A) that is introduced by this functionalization is preferably at least 0.002% by weight, more preferably at least 0.02% by weight, most preferably at least 0.03% by weight, and preferably at most 0.7% by weight, more preferably at most 0.32% by weight, most preferably at most 0.17% by weight.

Examples of hydrocarbyl radicals $R^1$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl-rest, dodecyl radicals such as the n-dodecyl radical, and octadecyl radicals such as the n-octadecyl radical; cycloalkyl radicals such as cyclopentyl, cyclohexyl, cycloheptyl and methylcyclohexyl radicals.

Preferred examples of $R^1$ are the methyl, ethyl, octyl and dodecyl radicals. A particularly preferred example of $R^1$ is the methyl radical.

Examples of hydrocarbyl radicals $R^2$ are the radicals as described for $R^1$ radical or a hydroxyl group —OH or an alkoxy group of the formula —O—$R^3$ where $R^3$ is a methyl, ethyl, n-propyl, isopropyl, 1-n-butyl, 2-n-butyl, isobutyl, tert-butyl, n-pentyl, isopentyl, neopentyl, or tert-pentyl radical, hexyl radicals such as the n-hexyl radical, heptyl radicals such as the n-heptyl radical, octyl radicals such as the n-octyl radical and isooctyl radicals such as the 2,2,4-trimethylpentyl radical.

Preferred examples of $R^2$ are the methyl radical, the ethyl radical, the hydroxyl group, the methoxy radical and the ethoxy radical.

Examples of $R^4$ are divalent hydrocarbyl radicals such as the methylene group, the 1,2-ethylene group, the 1,3-propylene group, the 1,3-butylene group, the 1,4-butylene group, the 1,5-pentylene group, and the 1,6-hexylene group.

Particularly preferred examples are the 1,3-propylene group and the 1,3-butylene group.

Examples of $R^5$ are divalent hydrocarbyl radicals such as the 1,2-ethylene group, the 1,3-propylene group, the 1,3-butylene group, the 1,4-butylene group, the 1,5-pentylene group, and the 1,6-hexylene group.

A particularly preferred example is the 1,2-ethylene group.

$R^6$ is preferably a hydrogen atom or a monovalent hydrocarbyl radical optionally substituted by —O— and having 1 to 10 carbon atoms, preferably having 1 to 6 carbon atoms, more preferably an alkyl or alkoxyalkyl radical having 1 to 10 carbon atoms, especially having 1 to 6 carbon atoms.

Preferred examples of the Y' radicals are
—$(CH_2)_2NH(CH_2)_2NH_2$,
—$(CH_2)_3NH(CH_2)_2NH_2$,
—$(CH_2)_3NH(CH_2)_3NH_2$,
—$(CH_2$—$CH(CH_3)$—$CH_2$—$)NH(CH_2)NH_2$ and
—$(CH_2)_4NH(CH_2)_4NH_2$.

Particularly preferred examples of the Y' radicals are
—$(CH_2)_3NH(CH_2)_2NH_2$, and
—$(CH_2$—$CH(CH_3)$—$CH_2$—$)NH(CH_2)NH_2$.

The indices k and m in formula (I') are chosen such that the viscosity of the amino-functionalized polydiorganosiloxanes (A') is preferably at least 50 mPas, more preferably at least 100 mPas, most preferably at least 250 mPas, measured in each case at 25° C. and a shear rate of 10/s, and preferably at most 100,000 mPas, more preferably at most 50,000 mPas, and most preferably at most 10,000 mPas, measured in each case at 25° C. and a shear rate of 5/s.

The ratio of k and m is chosen such that the amino-functionalized polydiorganosiloxanes (A') preferably have an amine value of at least 0.025 mmol/g, more preferably at least 0.075 mmol/g, most preferably at least 0.1 mmol/g, and preferably at most 0.4 mmol/g, more preferably at most 0.25 mmol/g, and most preferably at most 0.2 mmol/g.

The reaction of the amino-functionalized organopolysiloxanes (A') with cyclic carbonates reduces the amine value. The carbamato-functionalized organopolysiloxanes (A), especially carbamato-functionalized polydiorganosiloxanes (A), thus preferably have an amine value of at least 0 mmol/g, more preferably at least 0.02 mmol/g, and most preferably at least 0.04 mmol/g, and preferably at most 0.30 mmol/g, more preferably at most 0.20 mmol/g, and most preferably at most 0.10 mmol/g.

The cyclic carbonates used for preparation of the carbamato-functionalized polydiorganosiloxanes (A) are either commercially available or can be synthesized, for example as described in U.S. Pat. No. 3,642,858 A.

Typically, the cyclic carbonates used are 1,2-alkylene carbonates or alkoxyalkyl-substituted ethylene carbonates. Preferred cyclic carbonates are those carbonates where $R^6$ is a hydrogen atom or a monovalent hydrocarbyl radical, optionally substituted by —O— and having 1 to 10 carbon atoms, more preferably having 1 to 6 carbon atoms.

Examples are ethylene carbonate, 1,2-propylene carbonate, 1,2-butylene carbonate, 1,2-pentylene carbonate, 1,2-hexylene carbonate, 1,2-octylene carbonate, 1,2-dodecylene carbonate, 3-methyl-1,2-butylene carbonate, 3-methyl-1,2-pentylene carbonate, 3-ethyl-1,2-pentylene carbonate, 4-methyl-1,2-pentylene carbonate, 5-methyl-1,2-hexylene carbonate, 3-methoxy-1,2-propylene carbonate, 3-ethoxy-1,2-propylene carbonate, 3-n-propoxy-1,2-propylene carbonate, 4-methoxy-1,2-butylene carbonate, 4-ethoxy-1,2-butylene carbonate, S-methoxy-3-butylene carbonate, 5-methoxy-1,2-heptylene carbonate.

Preferred cyclic carbonates are ethylene carbonate, 1,2-propylene carbonate, and 3-methoxy-1,2-propylene carbonate. A particularly preferred cyclic carbonate is 1,2-propylene carbonate.

The nonionic, polyethylene oxide-containing emulsifiers (B) used in the aqueous emulsions of the invention are those preferably having an HLB value of not less than 16, more preferably not less than 17, and at the same time preferably a content of ethylene oxide units of preferably not less than 45, more preferably not less than 50, and preferably not more than 600, more preferably not more than 400, and most preferably not more than 250.

The HLB value (HLB stands for hydrophilic-lipophilic balance) describes the hydrophilic and lipophilic component of mainly nonionic surfactants. The HLB value can be calculated for nonionic surfactants according to Hans-Dieter Dörfler, Grenzflächen- and Kolloidchemie [Interfacial and Colloidal Chemistry], VCH, Weinheim, 1994, p. 198, as follows:

$$HLB = 20 \times \left(1 - \frac{M_1}{M}\right)$$

In this formula, $M_1$ is the molar mass of the lipophilic component of a molecule and M the molar mass of the whole molecule. The factor of 20 is a freely selected scaling factor.

Examples of the nonionic, polyethylene oxide-containing emulsifiers (B) of the invention are:
  alkyl polyglycol eaters, preferably those alkyl radicals of 8 to 20 carbon atoms, for example Steareth-100 (9005-00-9), Talloweth-50, Talloweth-80 (61791-28-4), Trideceth-50 (24938-91-8),
  carboxylic acid polyglycol esters, especially fatty acid polyglycol esters, preferably those carboxylic esters of 8 to 20 carbon atoms, for example PEG-75 oleate, PEG-200 oleate, PEG-300 monooleate, PEG-400 oleate, PEG-150 laurate, PEG-400 laurate, PEG-75 stearate, PEG-100 stearate, PEG-600 stearate, PEG-150 distearate,
  ethoxylated sorbitan fatty acid esters, for example PEG-40 sorbitan oleate, PEG-80 sorbitan laurate,
  ethoxylated castor oil or hydrogenated variants, for example (naming according to INCI nomenclature) PEG 75 Castor Oil or PEG200 Castor Oil or PEG-80 hydrogenated Castor Oil, PEG-100 hydrogenated Castor Oil, PEG-200 hydrogenated Castor Oil,
  ethoxylated fatty amines, for example PEG-100 tallowalkylamine (61791-44-4), PEG-40 stearylamine,
  ethoxylated glyceryl fatty acid carboxylates, for example PEG-40 glyceryl laurate, PEG-200 glyceryl stearate, PEG-200 glyceryl tallowate, PEG-200 hydrogenated glyceryl palmate,
  block copolymers of ethylene oxide and propylene oxide units (polyalkylene block polymers such as the so-called poloxamers), for example PEG-PPG-PEG block polymer Pluronic® F-108 (HLB >24; $M_n \approx 14\,600$) (available from Sigma-Aldrich),
  copolymers of ethylene oxide and propylene oxide units bridged via an ethylenediamine core (called poloxamines), for example Tetronic 1107 (HLB value: 24; $M_n \approx 15\,000$) (available from Sigma-Aldrich).

The nonionic, polyethylene oxide-containing emulsifiers (B) of the invention may consist of one of the abovementioned emulsifiers or of a mixture of two or more abovementioned emulsifiers, in which case they may be used in pure form or as solutions of one or more emulsifiers in water or organic solvents.

Further ingredients used in the emulsions of the invention may be
  (D) further ionic or nonionic emulsifiers or mixtures thereof, such as a combination of nonionic and cationic emulsifiers, each having an HLB value of less than 15.

Examples of anionic emulsifiers are:
1. Alkyl sulfates, particularly those having a chain length of 8 to 18 carbon atoms, alkyl and alkaryl ether sulfates having 8 to 18 carbon atoms in the hydrophobic radical and 1 to 30 ethylene oxide (EO) or propylene oxide (PO) units.
2. Sulfonates, particularly alkylsulfonates having 8 to 18 carbon atoms, alkylarylsulfonates having 8 to 18 carbon atoms, taurides, esters and monoesters of sulfosuccinic acid with monohydric alcohols or alkylphenols having 4 to 15 carbon atoms; these alcohols or alkylphenols may optionally also have been ethoxylated with 1 to 30 EO units.
3. Alkali metal and ammonium salts of carboxylic acids having 8 to 20 carbon atoms in the alkyl, aryl, alkaryl or aralkyl radical.
4. Partial phosphoric esters and the alkali metal and ammonium salts thereof, particularly alkyl- and alkaryl phosphates having 8 to 20 carbon atoms in the organic radical, alkyl ether or alkaryl ether phosphates having 8 to 20 carbon atoms in the alkyl or alkaryl radical and 1 to 30 EO units.

Examples of nonionic emulsifiers are:
5. Polyvinyl alcohol still having 5% to 50%, preferably 8% to 20%, vinyl acetate units, having a degree of polymerization of 500 to 3000.
6. Alkyl polyglycol ethers, preferably those having 3 to 30 EO units and alkyl radicals of 8 to 20 carbon atoms.
7. Alkylaryl polyglycol ethers, preferably those having 5 to 30 EO units and 8 to 20 carbon atoms in the alkyl and aryl radicals.
8. Ethylene oxide/propylene oxide (EO/PO) block copolymers, preferably those having 8 to 30 EO/PO units.
9. Addition products of alkylamines with alkyl radicals of 8 to 22 carbon atoms with ethylene oxide or propylene oxide.
10. Fatty acids having 6 to 24 carbon atoms.
11. Alkyl polyglycosides of the general formula $R^*$—O—$Z_o$ in which $R^*$ is a linear or branched, saturated or unsaturated alkyl radical having an average of 8-24 carbon atoms and $Z_o$ is an oligoglycoside radical having an average of o=1-10 hexose or pentose units or mixtures thereof.
12. Natural substances and derivatives thereof, such as lecithin, lanolin, saponins, cellulose; cellulose alkyl ethers and carboxyalkyl celluloses, the alkyl groups of which each have up to 4 carbon atoms.
13. Linear organo(poly)siloxanes containing polar groups, especially containing the elements O, N, C, S, P, Si, especially those having alkoxy groups having up to 24 carbon atoms and/or up to 40 EO and/or PO groups.

Examples of cationic emulsifiers are:
14. Salts of primary, secondary and tertiary fatty amines having 8 to 24 carbon atoms with acetic acid, sulfuric acid, hydrochloric acid and phosphoric acids.
15. Alkylpyridinium, alkylimidazolinium and alkyloxazolinium salts, especially those wherein the alkyl chain has up to 18 carbon atoms, especially the halides, sulfates, phosphates and acetates.
16. Quaternary alkyl- and alkylbenzeneammonium salts, especially those wherein the alkyl groups have 6 to 24 carbon atoms, especially the halides, sulfates, phosphates and acetates.

Examples of ampholytic emulsifiers are:
17. Amino acids having long-chain substitution, such as N-alkyldi(aminoethyl)glycine or N-alkyl-2-aminopropionic salts.
18. Betaines such as N-(3-acylamidopropyl)-N,N-dimethylammonium salts having a $C_8$-$C_{18}$-acyl radical and alkylimidazolium betaines.

Preferred emulsifiers are nonionic emulsifiers, especially the alkyl polyglycol ethers listed above under 6. The emulsifiers (D) may be used alone or in the form of a mixture of two or more abovementioned emulsifiers, in which case they may be used in pure form or as solutions of one or more emulsifiers in water or organic solvents.

The emulsions of the invention preferably contain emulsifiers (D) in amounts of at least 0.5% by weight, more preferably at least 1% by weight, especially at least 2% by weight, and preferably at most 20% by weight, more preferably at most 15% by weight, especially at most 10% by weight.

Further ingredients used in the emulsions of the invention may be
  (E) nonaqueous solvents or coemulsifiers.

The emulsions of the invention may contain
(E) nonaqueous solvents or coemulsifiers preferably in an amount of at least 0.1% by weight, more preferably at least 0.4% by weight, especially at least 0.8% by weight, and preferably at most 20% by weight, more preferably at most 15% by weight, especially at most 10% by weight.

The nonaqueous solvents (E) that may be used in the aqueous emulsions of the invention come from the group, for example, of the mono- or polyhydric alcohols, alkanolamines or glycol ethers. Examples of solvents are ethanol, n- or i-propanol, butanols such as 1-butanol, 2-butanol or 2-methyl-2-propanol, pentanols such as 1-pentanol, 2-pentanol or 3-pentanol, hexanols such as 1-hexanol, 2-hexanol or 3-hexanol, heptanols such as 1-heptanol, 2-heptanol, 3-heptanol or 4-heptanol, octanols such as 1-octanol, 2-octanol, 3-octanol or 4-octanol, glycol, propanediol, butanediols such as butane-1,2-diol or butane-1,3-diol, hexanediols such as hexane-1,2-diol or 2-methylpentane-2,4-diol, octanediols such as 2-ethylhexane-1,3-diol or octane-1,2-diol, glycerol, diglycol, propyl- or butyldiglycol, ethylene glycol methyl ether, ethylene glycol ethyl ether, ethylene glycol propyl ether, ethylene glycol mono-n-butyl ether, diethylene glycol methyl ether, diethylene glycol ethyl ether, diethylene glycol mono-n-butyl ether, propylene glycol methyl ether, propylene glycol ethyl ether, propylene glycol propyl ether, propylene glycol n-butyl ether, propylene glycol-tert-butyl ether, methoxytriglycol, ethoxytriglycol, butoxytriglycol, dipropylene glycol monomethyl ether, dipropylene glycol monoethyl ether, 1-butoxyethoxy-2-propanol or 3-methyl-3-methoxybutanol, 1-aminobutane, 2-aminobutane, 2-amino-2-methylpropane, 1-aminopentane, 2-aminopentane, 1-aminohexane, 1-aminoheptane and 1-aminooctane; ethyl acetate, propyl acetate, isopropyl acetate, butyl acetate, isobutyl acetate, pentyl acetate, isopentyl acetate and hexyl acetate; methyl propionate, ethyl propionate and tert-butyl propionate; methyl butyrate, ethyl butyrate, propyl butyrate and butyl butyrate; 2-butanone, 2-pentanone, 3-pentanone, 4-methyl-2-pentanone, 2-hexanone, 3-hexanone, 2-heptanone, 3-heptanone, 4-heptanone, 5-methyl-3-heptanone, 2-octanone and 3-octanone and mixtures of these cosurfactants. Examples of preferred nonaqueous solvents or coemulsifiers (E) are 1-alkanols from the above-adduced examples having $C_5$ to $C_8$ chains, alkanediols from the above-adduced examples having $C_4$ to $C_8$ chains, glycerol, propyl acetate, butyl acetate and pentyl acetate, 2-pentanone and the above-adduced ethylene glycol, propylene glycol, dipropylene glycol or diethylene glycol monoalkyl ethers.

Particularly preferred nonaqueous solvents or coemulsifiers (E) are 1-pentanol, 1-hexanol, 1-octanol, propanediol, butane-1,3-diol, hexane-1,2-diol, 2-ethylhexane-1,3-diol, octane-1,2-diol, glycerol, diethylene glycol methyl ether, diethylene glycol ethyl ether, diethylene glycol mono-n-butyl ether, or propylene glycol methyl ether.

In addition, it is possible to use polyalkylene glycols such as polyethylene glycols (e.g. PEG600, PEG1000 or PEG6000) or polypropylene glycols (e.g. PPG2000), polyalkylene block polymers having an HLB value of less than 15, such as the so-called poloxamers (block copolymers of ethylene oxide and propylene oxide units), for example PEG-PPG-PEG block polymer Pluronic® L-31, PEG-PPG-PEG block polymer Pluronic® L-61, PPG-PEG-PPG block polymer Pluronic® 17R4, PPG-PEG-PPG Pluronic® block polymer 31R1 (HLB in each case <7) (available from Sigma-Aldrich) or else poloxamines (copolymers of ethylene oxide and propylene oxide units bridged via an ethylenediamine core) having an HLB value of less than 15, for example Tetronic 701 or Tetronic 90R4 (HLB in each case <7) (available from Sigma-Aldrich) as coemulsifiers.

Further ingredients used in the emulsions of the invention may be
(F) auxiliaries such as pH regulators, salts, foam inhibitors, thickeners and/or protective colloids, preservatives, disinfectants, wetting agents, corrosion inhibitors, dyes, fragrances or mixtures thereof.

Usable pH regulators here are all known acids or alkalis, provided that their use is not forbidden for application-related or environmental reasons or for reasons of consumer protection.

The acids used serve to establish a desired pH or may form acid addition salts with the amino-containing radicals (Y) of the carbamato-functionalized polydiorganosiloxanes (A).

Examples of mineral acids which can be reacted with the aforementioned amino-containing radicals (Y), for example, are hydrochloric acid, perchloric acid, sulfuric acid, sulfurous acid, nitric acid, nitrous acid, hydrofluoric acid, phosphoric acids, diphosphoric acids and polyphosphoric acids. Examples of suitable carboxylic acids are formic acid, acetic acid, propionic acid, butanoic acids, citric acid, trichloric acetic acid, dichloric acetic acid and chloroacetic acid, trifluoroacetic acid, cyanoacetic acid, phenylacetic acid, benzoic acid, m- and p-nitrobenzoic acid, oxalic acid, malonic acid and lactic acid.

Particular preference is given to acetic acid and formic acid.

In the context of the present invention, the pH is measured with an electrode in accordance with US Pharmacopeia USP 33 at 20° C.

Examples of salts (electrolytes) are especially those from the group of the inorganic salts, it being possible to use a large number from a variety of different salts. Preferred cations are the alkali metals and alkaline earth metals; preferred anions are the halides and sulfates. From a production point of view, preference is given to the use of sodium acetate or sodium chloride in the aqueous emulsions of the invention.

Examples of foam inhibitors are soaps, paraffins or silicone oils.

Examples of preservatives are methylisothiazolinone, chloromethylisothiazolinone, benzylisothiazolinone, phenoxyethanol, methylparaben, ethylparaben, propylparaben, butylparaben, isobutylparaben, alkali metal benzoates, alkali metal sorbates, iodopropynyl butyl carbamate, benzyl alcohol and 2-bromo-2-nitropropane-1,3-diol.

The emulsification of the carbamato-functionalized polydiorganosiloxanes (A) of the invention with the aid of the nonionic, polyethylene oxide-containing emulsifiers (B) of the invention is effected by vigorously commixing the carbamato-functionalized polydiorganosiloxanes (A) in water (C) with the emulsifiers (B), optionally the emulsifiers (D), optionally the nonaqueous solvents or coemulsifiers (E), optionally the further auxiliaries (F). Stable emulsions are formed, in which the carbamato-functionalized polydiorganosiloxanes (A) are in finely divided form. The emulsifying operation for production of the inventive aqueous emulsions of carbamato-functionalized polydiorganosiloxanes (A) is preferably conducted at temperatures of at least 10° C., more preferably at least 15° C. and preferably at most 80° C., more preferably at most 70° C.

The increase in temperature preferably occurs through the introduction of mechanical shear energy which is required for the emulsification process. The increase in temperature is not required to accelerate any chemical process. Moreover, the process of the invention is preferably conducted at the pressure of the surrounding atmosphere, but can also be conducted at higher or lower pressures.

The production may be continuous or batchwise.

Technologies for production of emulsions of organopolysiloxanes are known. Thus, the vigorous mixing and dispersing can be effected in rotor-stator stirrer apparatuses, colloid mills, high-pressure homogenizers, microchannels, membranes, jet nozzles and the like, or by means of ultrasound. Homogenizing equipment and processes are described, for example, in Ullmann's Encyclopedia of Industrial Chemistry, CD-ROM edition 2003, Wiley-VCH Verlag, under "Emulsions".

The way in which the components that are used for production of the emulsions of the invention are mixed is not very critical and can be executed in varying sequence. Depending on the components (A), (B), optionally (D), optionally (E) and optionally (F), however, preferred procedures may arise and should be examined in the individual case.

For example, the initial charge may comprise component (A) and optionally an acid (F') and then the emulsifiers (B) and optionally (D) and optionally the coemulsifiers (E) are added and then the dispersant water (C) and optionally further auxiliaries (F) are incorporated. In many cases, it has been found that it is advantageous to include the emulsifiers (B), optionally emulsifiers (D) and optionally coemulsifiers (E) and optionally an acid (F') as auxiliary together with a portion of the dispersant water (C) in the initial charge in the emulsification apparatus, and to incorporate component (A) and the further components into this mixture obtained.

The invention further provides cosmetic compositions comprising,
in a cosmetically acceptable medium, preferably water,
at least one hair conditioner and
at least one aqueous emulsion of the invention.

The invention further provides a method for treatment of keratinic fibers, preferably hair, with the cosmetic compositions of the invention.

Preferably, these compositions are cosmetic compositions which have the task of washing and care of hair. Examples of compositions for washing and care of hair are hair shampoos, rinse-off conditioners, hair tonics, hair masks, hair serums, hair foams, hairstyling sprays, hair creams, hair gels, hair. oils, hair end fluids and hair colorants.

"Care" in this connection means keeping the keratinic fibers in their original form, to reduce or to avoid the effects of outside influences (e.g. time, light, temperature, pressure, soiling, chemical reaction with other reactive compounds that come into contact with the article), for example aging, soiling, bleaching, or even to improve desired positive properties of keratinic fibers. Examples of these are improvement of softness and smoothness, reduction of combing forces, shine properties, improvement of color impressions, color protection properties, reduction of electrostatic charges, protection properties under thermal stress on the hair or hydrophobization.

The aqueous emulsions of the invention are preferably used in these compositions in amounts of 0.1% to 40% by weight, more preferably of 0.2% to 30% by weight, especially 0.4% to 20% by weight, based in each case on the total weight of the compositions.

The composition in which the aqueous emulsions of the invention are used may be in the form of a W/O emulsion (water-in-oil emulsion), an O/W emulsion (oil-in-water emulsion) or of a multiple emulsion.

Preferably, the cosmetically acceptable medium in the cosmetic composition is water.

The compositions in which the aqueous emulsions of the invention are used are preferably compositions having a translucent or transparent appearance.

These preferred compositions are transparent or translucent microemulsions having a droplet diameter in the range from about 0.01 µm to about 0.1 µm.

By contrast, in simple emulsions, in one phase, there are finely dispersed droplets of the second phase ensheathed by an emulsifier shell (water droplets in W/O or lipid vesicles in O/W emulsions). The droplet diameters of the standard emulsions are in the range from about 1 µm to about 50 µm. Such "macroemulsions" are, without further coloring additions, milky white in color and opaque. Finer "macroemulsions", the droplet diameters of which are in the range from about 0.1 µm to about 1 µm, again without coloring additions, are bluish white in color and opaque.

Only micellar and molecular solutions having particle diameters of less than about 0.01 µm have a clear and transparent appearance.

The cosmetic compositions in which the aqueous emulsions of the invention are used contain at least one hair conditioner, referred to hereinafter simply as conditioner. Analogously to K. Krummel, Stephane Chiron, J. Jachowicz, Chapter 14, in: "The Chemistry and Manufacture of Cosmetics", Volume II, Formulating, Third Edition by Mitchell L. Schlossmann, 2000, p. 359-396, conditioners refer to cosmetic ingredients which modify the hair surface and affect the characteristics of the hair. Cosmetic compositions comprising conditioners are used to modify or improve the softness of the hair, for better disentanglability, for reduction in wet and dry combing force, for haircare, for avoidance of electrostatic charging, for smoother gliding through the hair and along the hair surface, for improvement of hair shine, for retention of colorfastness of hair, for reduction of hair breakage, for retention of the hairstyle and further cosmetic properties that are connected to natural and healthy hair.

The composition in which the aqueous emulsions of the invention are used improves one or more of the abovementioned effects.

Examples of conditioners and the INCI names thereof are described in the "International Cosmetic Ingredient Dictionary and Handbook" from the Personal Care Product Council (eds.). A reference that may be used is the Worldwide Web-based "wINCI" Web Based International Cosmetic Ingredient Dictionary and Handbook (http://online.personalcarecouncil.org/jsp/Home.jsp) or the International Cosmetic Ingredient Dictionary and Handbook, 13th Edition, The Personal Care Products Council (formerly: The Cosmetic, Toiletry, and Fragrance Association (CTFA)), 2010.

Preferred examples of conditioners are cationic polymers. These are understood to mean polymers that bear pendent or terminal cationic groups or pendent or terminal groups that can be converted to a cationic group by ionization. Preference is given to using cationic polymers having a quaternary ammonium group.

Examples of cationic polymers used with preference are published in the International Cosmetic Ingredient Dictionary and Handbook under the "Polyquaternium" name, each polymer being identified by an individual numeric code, for example Polyquaternium-1.

Further examples of cationic polymers are derivatives of modified polysaccharides having quaternary ammonium groups, for example polymers having the INCI names Cassia Hydroxypropyltrimonium Chloride, derivatives of modified cellulose and/or starch, for example a quaternary ammonium derivative of a propylene glycol ether-modified Cyamopsis tetragonoloba (guar) gum having the INCI name Guar Hydroxypropyltrimonium Chloride, or polymeric quaternary ammonium salts of the reaction product of hydroxyethyl cellulose with a trimethylammonium-substituted epoxide, such as cellulose, 2-hydroxyethyl 2-(2-hydroxy-3-(trimethylammonium)propoxy)ethyl 2-hydroxy-3-(trimethylammonium)propyl ether chloride, such as cellulose, 2-hydroxyethyl 2-hydroxy-3-(trimethylammonium)propyl ether, chloride, such as cellulose, 2-hydroxyethyl 2-hydroxy-3-(trimethylammonium)propyl ether, chloride, such as cellulose, 2-[2-hydroxy-3-(trimethylammonium)propoxy]ethyl ether, chloride, with the INCI name Polyquaternium-10.

Further examples of cationic polymers are the following cationic polymers having quaternary ammonium groups: acrylic acid polymer derivatives, acrylic acid copolymer derivatives, methacrylic acid derivatives and methacrylic acid copolymer derivatives, for example polymers having the INCI name Polyquaternium-37.

Further examples of cationic polymers are copolymers having quaternary ammonium groups that are formed from dimethyldiallylammonium chloride and acrylic acid, for example polymers having the INCI name Polyquaternium-22.

Further examples of cationic polymers are copolymers having quaternary ammonium groups that are formed from derivatives of vinylpyrrolidone, vinylimidazole and vinylimidazoline and methacrylic acid, for example polymers having the INCI name Polyquaternium-86.

Further examples of cationic polymers are copolymers having quaternary ammonium groups that are formed from acrylamide and dimethyldiallylammonium chloride, for example polymers having the INCI name Polyquaternium-7.

Further examples of cationic polymers are copolymers having quaternary ammonium groups that are formed from the reaction product of diethyl sulfate with vinylpyrrolidone and dimethylaminoethyl methacrylate, for example polymers having the INCI name Polyquaternium-11.

The composition in which the aqueous emulsions of the invention are used contains cationic polymers preferably in amounts of 0.01% to 5% by weight, more preferably of 0.05% to 4% by weight, especially 0.10% to 3% by weight, based in each case on the total weight of the composition.

Further preferred examples of conditioners are cationic surfactants. Examples of cationic surfactants used with preference correspond to the materials listed in points 14. to 16. under examples of cationic emulsifiers. Examples are cetyltrimethylammonium salts or behenyltrimethylammonium salts. Examples of anionic counterions that may be present include chloride, bromide, methosulfate. INCI names of cationic surfactants used with preference are, for example, Cetrimonium Chloride, Cetrimonium Methosulfate, Behentrimonium Chloride, Behentrimonium Methosulfate, Steartrimonium Bromide.

The composition in which the aqueous emulsions of the invention are used preferably contains cationic surfactants in amounts of 0.1% to 7% by weight, more preferably of 0.15% to 6% by weight, especially 0.2% to 5% by weight, based in each case on the total weight of the composition.

Further examples of conditioners are nonpolymeric quaternary ammonium compounds. This is understood to mean nonpolymeric ammonium compounds that are in cationic form or can be converted to a cationic group by ionization. Examples of nonpolymeric quaternary ammonium compounds used with preference are dimethyldioctadecylammonium chloride having the INCI name Distearyldimonium Chloride, N-[3-(dimethylamino)propyl]-octadecanamide having the INCI name Stearamidopropyl Dimethylamine or compounds having the INCI name Dicocoylethyl Hydroxyethylmonium Methosulfate or Quaternium-87.

Further preferred examples of conditioners are organopolysiloxanes and organopolysiloxane copolymers other than the carbamato-functionalized polydiorganosiloxanes (A) present in the aqueous emulsions of the invention. The organopolysiloxanes may be in the form of an oil, wax, gum or resin, or in the form of an emulsion.

Examples of such organopolysiloxanes other than carbamato-functionalized polydiorganosiloxanes (A) are:
cyclic organopolysiloxanes of the formula $[R^*_2SiO]_x$
where x is an integer from 4 to 8,
linear organopolysiloxanes of the general formula

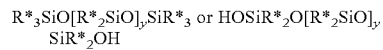

where y is 0 or an integer from 1 to 2000, and
resinous organopolysiloxanes of the general formula $R^*_tSiO_{(4-t)/2}$ where each $R^*$ has the definition given above for $R^1$ or $Y'$ and t is 0, 1, 2 or 3,
such that the organopolysiloxane resin is formed from M, D, T and/or Q units, preference likewise being given to the combination predominantly or exclusively composed of D and T units, such as the combination predominantly or exclusively composed of M and Q units, where, in the case of the resins formed predominantly or exclusively from D and T units, T units are preferably in a molar ratio of T/[M+D+T+Q] of 0.45 to 1, more preferably of 0.55 to 1.0, and the number of M and Q units in both cases is preferably zero and in which, in the case of the organopolysiloxane resins formed predominantly or exclusively from M and Q units, Q units are preferably in a molar ratio Q/[M+D+T+Q] of 0.25 to 0.9, more preferably of 0.35 to 0.7, and the number of D and T units in both cases is preferably zero.

Examples of organopolysiloxanes, in the present case in the form of an oil, are polydimethylsiloxanes having the viscosity of 0.65 to 2,000,000 mPas (25° C.) and the INCI names Disiloxane and Dimethicone.

Further examples of organopolysiloxanes, in the present case in the form of an oil or wax, are functionalized organopolysiloxanes, for example polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

Further examples of organopolysiloxanes are silicone resins having the INCI names Trimethylsiloxysilicate or Polymethylsilsesquioxane.

The composition in which the aqueous emulsions of the invention are used comprises organopolysiloxanes and organopolysiloxane copolymers other than the carbamato-functionalized polydiorganosiloxanes (A), preferably in amounts of 0.1% to 40% by weight, preferably of 0.2% to 30% by weight, especially 0.3% to 20% by weight, based in each case on the total weight of the composition.

Further preferred examples of conditioners are fatty acid esters and fatty acid alcohols.

Examples of fatty acid alcohols are alcohols having $C_8$-$C_{28}$ carbon chains, such as the fatty alcohols 1-octadecanol having the INCI name Stearyl Alcohol, 1-hexadecanol having the INCI name Cetyl Alcohol, or fatty alcohols having INCI names Cetearyl Alcohol, Myristyl Alcohol, Caprylic Alcohol, Lauryl Alcohol, Decyl Alcohol and Oleyl Alcohol.

In addition to conditioning properties, fatty acid alcohols also fulfill a structuring, thickening effect in cosmetic compositions.

Further examples of fatty acid esters are esters of the fatty acids having the INCI names Palmitic Acid, Oleic Acid, Linolic Acid, Linoleic Acid, Caprylic Acid, Myristic Acid, Stearic Acid, for example fatty acid esters having the INCI names Isopropyl Palmitate, Ethylhexyl Palmitate, Isopropyl Myristate, Isopropyl Stearate.

The composition in which the aqueous emulsions of the invention are used contains fatty acid esters and fatty acid alcohols preferably in amounts of 0.1% to 15% by weight, more preferably of 0.3% to 12% by weight, especially 0.5% to 10% by weight, based in each case on the total weight of the composition.

Further preferred examples of conditioners are natural or synthetic oils and waxes.

Examples of preferred oils and waxes are hydrocarbons having linear or branched, saturated or unsaturated $C_4$-$C_{60}$ carbon chains, such as oils and waxes having the INCI names Isododecane, hydrated Polyisobutylene, hydrated Polydecene, Paraffin and Isoparaffin.

Further examples of preferred oils and waxes are carnauba wax, beeswax, wool wax, microcrystalline wax, jojoba oil, rice oil, calendula oil, sunflower oil, soybean oil, coconut oil, olive oil and almond oil.

The composition in which the aqueous emulsions of the invention are used contains oils and waxes preferably in amounts of 0.1% to 10% by weight, more preferably of 0.2% to 7% by weight, especially 0.3% to 5% by weight, based in each case on the total weight of the composition.

Further preferred examples of conditioners are panthenol, lipids such as ceramides, proteins and hydrolyzed proteins, such as hydrolyzed collagen, hydrolyzed wheat proteins and hydrolyzed silk.

Hair conditioners used are preferably those selected from the group of
cationic polymers,
cationic surfactants,
nonpolymeric quaternary ammonium compounds,
organopolysiloxanes and organopolysiloxane copolymers other than the carbamato-functionalized polydiorganosiloxanes (A) present in the aqueous emulsions of the invention,
fatty acid esters and fatty acid alcohols,
natural or synthetic oils and waxes and
panthenol, lipids, proteins and hydrolyzed proteins, and mixtures thereof.

Optionally, the composition comprises further standard cosmetic additives, for example surfactants, thickeners, gelating agents, film formers, humectants, UV filters, pearlescent pigments, vitamins, antioxidants, caffeine, active antidandruff ingredients or preservatives, or mixtures thereof.

Examples of further additives customary in cosmetics and the INCI names thereof are described in the "International Cosmetic Ingredient Dictionary and Handbook" from the Personal Care Product Council.

Optionally, the composition comprises further standard cosmetic additives such as surfactants.

Examples of surfactants customary in cosmetics are also described in K. Schrader, A. Domsch, Cosmetology—Theory and Practice, Volume II, pages II-8 to II-22, Verlag für chemische Industrie, 2005, and in points 1. to 18. under examples of emulsifiers.

Examples of anionic surfactants used with preference correspond to the materials listed in points 1. to 3. under examples of anionic emulsifiers.

INCI names of anionic surfactants used with preference are, for example, Sodium Lauryl Sulfate, Ammonium Laureth Sulfate, Sodium Laureth Sulfate, Disodium 2-Sulfolaurate, Disodium Lauryl Sulfosuccinate or Disodium Laureth-Sulfosuccinate.

The composition in which the aqueous emulsions of the invention are used contains anionic surfactants preferably in amounts of 1% to 30% by weight, more preferably of 5% to 25% by weight, especially 7% to 20% by weight, based in each case on the total weight of the composition.

Examples of nonionic surfactants used with preference correspond to the materials listed in points 5. to 13. under examples of nonionic emulsifiers. INCI names of nonionic surfactants used with preference are, for example, Coco Glucoside, Lauryl glucoside, Decyl Glucoside, PEG-40 Hydrogenated castor oil, Polysorbate 80 or PEG-7 Glyceryl Cocoate.

The composition in which the aqueous emulsions of the invention are used contains nonionic surfactants preferably in amounts of 1% to 15% by weight, more preferably of 2% to 12% by weight, especially 3% to 10% by weight, based in each case on the total weight of the composition.

Examples of amphoteric surfactants used with preference correspond to the materials listed in points 17. to 18. under examples of nonionic emulsifiers. Further preferred examples are compounds from the classes of the alkylamido betaines, alkyl amphoacetates and alkyl amphopropionates. INCI names of nonionic surfactants used with preference are, for example, Cocamidopropyl Betaine, Cetyl Betaine, Cocamide MEA, Cocamide DEA, Cocamide MIPA, Sodium Cocoamphoacetate and Sodium Cocoamphopropionate.

The composition in which the aqueous emulsions of the invention are used contains amphoteric surfactants preferably in amounts of 1% to 15% by weight, more preferably of 2% to 12% by weight, especially 3% to 10% by weight, based in each case on the total weight of the composition.

Optionally, the composition comprises further standard cosmetic additives such as thickeners.

Examples of thickeners used with preference are modified polysaccharides such as starch, cellulose, gum arabic and guar gums, for example polymers having the INCI name Cellulose Gum, Guar Gum, Xanthan Gum or Cassia Gum.

Further examples of thickeners are hydrophobically modified nonionic cellulose derivatives, for example the cellulose derivative having the INCI name Hydroxyethylcellulose.

Further examples of thickeners are crosslinked acrylic acid and methacrylic acid polymers and derivative of the crosslinked acrylic acid or methacrylic acid polymers, for example polymers having the INCI name Carbomer.

Further examples of thickeners are agents that, in combination with surfactants, achieve a thickening effect. Examples are monoglycerides of fatty acids, mono/diglycerides of ethoxylated fatty acids and ethoxylated fatty alcohols. INCI names of thickeners used with preference that achieve a thickening effect in combination with surfactants are PEG-120 Methyl Glucose Dioleate, PEG-150 Distearate, Myristyl Glycol, PEG-200 Glyceryl Palmitate, Laureth-4 or PEG-200 Glyceryl Palmitate.

Further examples of thickeners are salts, for example salts having the INCI name Sodium Chloride.

The composition in which the aqueous emulsions of the invention are used contains thickeners preferably in amounts of 0.1% to 10% by weight, based in each case on the total weight of the composition.

Optionally, the composition comprises further standard cosmetic additives such as film formers.

Preferred examples of film formers are polymers.

Examples of film-forming polymers used with preference are described in the "International Cosmetic Ingredient Dictionary and Handbook" from the Personal Care Product Council.

Examples of preferred film-forming polymers are acrylic acid polymer derivatives, acrylic acid copolymer derivatives, methacrylic acid derivatives and methacrylic acid copolymer derivatives. Examples of preferred anionic polymers are copolymers of vinyl acetate and one or more acrylic or methacrylic acid monomers and esters thereof, for example polymers having the INCI name Acrylates/VA Copolymer.

Further examples of preferred film-forming polymers are copolymers of vinylpyrrolidone and one or more acrylic or methacrylic acid monomers and esters thereof, for example polymers having the INCI name Acrylates/VP Copolymer.

Further examples of preferred film-forming polymers are copolymers of tert-butylacrylamide and one or more acrylic or methacrylic acid monomers and esters thereof, for example polymers having the INCI name Acrylates/t-Butylacrylamide Copolymer.

Further examples of preferred film-forming polymers are copolymers of vinyl acetate, crotonic acid and vinyl neodecanoate monomers, for example polymers having the INCI name VA/Crotonates/Vinyl Neodecanoate Copolymer.

Further examples of preferred film-forming polymers are copolymers of vinyl acetate, crotonic acid and vinyl neodecanoate monomers and vinylsilicones, for example polymers having the INCI name Crotonic Acid/Vinyl C8-C12 Isoalkyl Esters/VA/Bis-Vinyldimethicone Copolymer.

The composition in which the aqueous emulsions of the invention are used contains film-forming polymers preferably in amounts of 0.1% to 15% by weight, more preferably of 0.2% to 10% by weight, especially 0.3% to 7% by weight, based in each case on the total weight of the composition.

Optionally, the composition comprises further standard cosmetic additives such as humectants.

Examples of humectants used with preference are glycerol, sorbitol, xylitol, polyethylene glycol, propane-1,2-diol, propane-1,3-diol or polypropylene glycol.

The composition in which the aqueous emulsions of the invention are used contains humectants preferably in amounts of 0.1% to 10% by weight, more preferably of 0.2% to 8% by weight, especially 0.3% to 6% by weight, based in each case on the total weight of the composition.

Optionally, the composition comprises further standard cosmetic additives such as pearlizing agents.

Examples of pearlizing agents used with preference are pearlescent pigments or glycol distearate.

The composition in which the aqueous emulsions of the invention are used preferably contains pearlizing agents in amounts of 0.1% to 7% by weight, more preferably of 0.2% to 6% by weight, especially 0.3% to 5% by weight, based in each case on the total weight of the composition.

The invention further provides a process for producing the cosmetic compositions, preferably the transparent cosmetic compositions, by mixing at least one aqueous emulsion of the invention with at least one hair conditioner and optionally further standard cosmetic additives in a cosmetically acceptable medium.

The individual ingredients may be mixed with one another in a hot/hot, hot/cold or cold/cold method.

The aqueous emulsion of the invention is added in the production of the cosmetic compositions of the invention preferably at temperatures of at most 50° C., more preferably at temperatures of at most 40° C., especially at temperatures of at most 35° C. It is preferably added at temperatures of at least 5° C., preferably at temperatures of at least 10° C.

In the examples which follow, all figures for parts and percentages, unless stated otherwise, are based on weight. Unless stated otherwise, the examples which follow are conducted at a pressure of the surrounding atmosphere, i.e. at about 1000 hPa, and at room temperature, i.e. about 20° C., or a temperature which is established on combination of the reactants at room temperature without additional heating or cooling.

The viscosities were measured on an "MCR 302" rheometer from Anton Paar according to DIN EN ISO 3219: 1994 and DIN 53019, using a cone-plate system (CP50-2 cone) with an opening angle of 2°. The instrument was calibrated with Normal oil 10000 from the Physikalisch-Technischen Bundesanstalt [German National Metrology Institute]. The measurement temperature is 25.00° C. +/−0.05° C., the measurement time 3 min. The viscosity figure is the arithmetic mean of three independently conducted individual measurements. The measurement uncertainty of the dynamic viscosity is 1.5%. The shear rate gradient was chosen as a function of the viscosity and is given separately for each viscosity figure.

The amine value states how many mmol of KOH are equivalent to 1 g of the substance to be determined. The amine value is determined according to DIN 16945-Version 1989-03.

1H NMR spectra are recorded as a solution in $CDCl_3$ on a Bruker Avance 500 NMR spectrometer (5 mm selective 1H NMR sample head) with a measurement frequency of 500.13 MHz.

The evaluation is effected as known to one skilled in the art and described in the following literature: "Über die 1H—, 13C— und 29Si-NMR chemischen Verschiebungen einiger linearer, verzweigter and cyclischer Methyl-Siloxan-Verbindungen" [On the 1H, 13C and 29Si Chemical Shifts of Some Linear, Branched and Cyclic Methylsiloxane Compounds], G. Engelhardt, H. Jancke; J. Organometal. Chem. 28 (1971), 293-300; "Chapter 8—NMR spectroscopy of organosilicon compounds", Elizabeth A. Williams, The Chemistry of Organic Silicon Compounds, 1989 John Wiley and Sons Ltd, 511-533.

The particle sizes were determined on a Zetasizer Nano-S particle sizer, from Malvern, Software Version 6.01, by means of dynamic light scattering (Mie analysis method). For this purpose, the emulsions were diluted to 0.5% by weight with filtered and degassed water. The values reported are always based on the D(50) value. D(50) should be considered to be the volume-averaged particle diameter at which 50% of all the particles measured have a volume-average diameter smaller than the D(50) value given.

EXAMPLES

Example 1: Carbamato-Functionalized Polydimethylsiloxane 1

1000.0 g of a reactively terminated copolymer composed of aminoethylaminopropylmethylsiloxane and dimethylsiloxane units, of viscosity 4320 mPas (at 25° C. and at a shear rate of 10 1/s) and of amine value 0.135 mmol/g, are initially charged in a 2000 ml three-neck flask under a nitrogen atmosphere, and 3.62 g of propylene carbonate are added. The reaction mixture is stirred at 50° C. for 2 hours and at 60° C. for two hours. After cooling, a clear product 1 of viscosity 6200 mPas (at 25° C. and at a shear rate of 10 1/s) is obtained. The 1H NMR spectrum shows a degree of functionalization with respect to carbamate of 25% of all amine groups available and hence 0.058% by weight of hydroxyl groups. The carbamato-functionalized polydimethylsiloxane 1 has an amine value of 0.10 mmol/g.

Example 2: Carbamato-Functionalized Polydimethylsiloxane 2

1000.0 g of a reactively terminated copolymer composed of aminoethylaminopropylmethylsiloxane and dimethylsiloxane units, of viscosity 4320 mPas (at 25° C. and at a shear rate of 10 1/s) and of amine value 0.135 mmol/g, are initially charged in a 2000 ml three-neck flask under a nitrogen atmosphere, and 7.24 g of propylene carbonate are added. The reaction mixture is stirred at 50° C. for 2 hours and at 60° C. for two hours. After cooling, a clear product 1 of viscosity 9480 mPas (at 25° C. and at a shear rate of 10 1/s) is obtained. The 1H NMR spectrum shows a degree of functionalization with respect to carbamate of 47% of all amine groups available and hence 0.107% by weight of hydroxyl groups. The carbamato-functionalized polydimethylsiloxane 2 has an amine value of 0.07 mmol/g.

(Comparative) Example V3: Amino-Functionalized Polydimethylsiloxane V3

This is a reactively terminated copolymer V3 of 3-(2-aminoethylamino)propylmethylsiloxy and dimethylsiloxy units having an amine value of 0.13 mmol/g and a viscosity of 3900 mPas (at 25° C. and at a shear rate of 10 1/s).

Example 4: Emulsion E1 of Carbamato-Functionalized Polydimethylsiloxane 1

An Ultra-Turrax T 50 emulsifying apparatus (from Janke & Kunkel/IKA) is initially charged with 12.0 g of isotridecyl hexaethoxylate, commercially available under the Imbentin T/060 trade name (from Kolb), 7.5 g of PEG-200 hydrogenated glyceryl palmate (HLB >19; 200 ethylene oxide units), commercially available under the Rewoderm LI 520-70 trade name (from Evonik) and 8.0 g of demineralized water. 30.0 g of the carbamato-functionalized product 1 is added in one portion at a shear rate of 4000 rpm, so as to result in a relatively firm, stiff phase as preliminary emulsion. 2.3 g of 80% acetic acid are added and the mixture is diluted with 90.93 g of demineralized water in portions under low shear to give the desired emulsion. The emulsion is preserved with 1.35 g of 2-phenoxyethanol. The result is a clear, colorless, pale bluish-shimmering, free-flowing emulsion E1 having a particle size D(50) of 32 nm. The emulsion is homogeneous and stable even after storage at room temperature for 6 months.

Example 5: Emulsion E2 of Carbamato-Functionalized Polydimethylsiloxane 2

Carbamato-functionalized polydimethylsiloxane 2 is emulsified by the same method as in example 4. The result is likewise a clear, colorless, pale bluish-shimmering, free-flowing emulsion E2 having a particle size D(50) of 30 nm. The emulsion is homogeneous and stable even after storage at room temperature for 6 months.

Examples 6-10: Emulsions E3 to E7 composed of the carbamato-functionalized polydimethylsiloxane 2 with different emulsifiers and amounts of emulsifier The emulsions which follow are prepared by the same method as described in example 4.

The following emulsifiers/amounts of emulsifier were used:

Example 6

12.0 g of isotridecyl hexaethoxylate, commercially available under the Imbentin T/060 trade name (from Kolb) 3.75 g of PEG-200 hydrogenated glyceryl palmate (HLB >19; 200 ethylene oxide units), commercially available under the Rewoderm LI 520-70 trade name (from Evonik) 3.75 g of glycerol The result is a clear, colorless, pale bluish-shimmering, free-flowing emulsion E3 having a particle size D(50) of 21 nm.

Example 7

12.0 g of isotridecyl hexaethoxylate, commercially available under the Imbentin T/060 trade name (from Kolb) 2.25 g of PEG-200 castor oil (50% aqueous solution) (HLB=18.1; 200 ethylene oxide units), commercially available under the Cirrasol G-1300 trade name (from Croda)

The result is a clear, pale bluish, readily free-flowing emulsion E4 having a particle size D(50) of 25 nm.

Example 8

12.0 g of isotridecyl hexaethoxylate, commercially available under the Imbentin T/060 trade name (from Kolb) 7.25 g of PEG-200 castor oil (50% aqueous solution) (HLB=18.1; 200 ethylene oxide units), commercially available under the Cirrasol G-1300 trade name (from Croda)

The result is a clear, bluish-shimmering, readily free-flowing emulsion E5 having a particle size D(50) of 22 nm.

Example 9

12.0 g of isotridecyl hexaethoxylate, commercially available under the Imbentin T/060 trade name (from Kolb) 3.45 g of PEG-100 stearate (HLB=18.8; 100 ethylene oxide units), commercially available under the Sympatens-BS/1000G trade name (from Kolb)

The result is a clear, bluish-shimmering, readily free-flowing emulsion E6 having a particle size D(50) of 28 nm.

Example 10

12.0 g of isotridecyl hexaethoxylate, commercially available under the Imbentin T/060 trade name (from Kolb) 7.50 g of PEG-80 sorbitan laurate (HLB=19.1; 80 ethylene oxide units), commercially available under the Tween 28 trade name (from Croda)

The result is a clear, bluish-shimmering, readily free-flowing emulsion E7 having a particle size D(50) of 22 nm.

(Comparative) Example 11

Emulsion CE1 of Carbamato-Functionalized Polydimethylsiloxane 2

Carbamato-functionalized polydimethylsiloxane 2 is emulsified by the same method as in example 4. But the emulsifiers used are 12.38 g of Laureth-4 (HLB=9.7; 4 ethylene oxide units), commercially available under the Sympatens ALM/040 trade name (from Kolb), and 7.13 g of Laureth-23 (HLB=16.9 but 23 ethylene oxide units), commercially available under the Sympatens ALM/230 G trade name (from Kolb). The result is a whitish, cloudy, free-flowing emulsion VE1 having a particle size D(50) of 112 nm.

Comparative example 11 shows that, when nonionic, polyethylene oxide-containing emulsifiers having a content of polyethylene oxide units of less than 40 are used, even when the HLB value is greater than 15, it is not possible to obtain emulsions of the invention having a particle size of not more than 100 nm.

(Comparative) Example 12

Emulsion VE2 of amino-functionalized polydimethylsiloxane V3 With the aid of an LDV 1 dissolver from PC Laborsystem, 6.5 g of isotridecyl pentaethoxylate, commercially available under the Lutensol TO 5 trade name (from BASF), 20.0 g of the amino-functionalized polydimethylsiloxane V3, 2.9 g of glycerol, 0.12 g of 80% acetic acid, 0.19 g of N-morpholinomethyl-triethoxysilane and 70 g of water are used to prepare an emulsion having an average particle size (D50) of 20 to 50 nm. 0.13 g of 2-phenoxyethanol is mixed into this emulsion.

Test Methods for Assessing the Effect of Cosmetic Compositions

The application characteristics of the cosmetic composition and the effect thereof with regard to combing force and softness are assessed on Caucasian hair. All hair tresses are washed before use. For this purpose, the hair tresses are placed into a solvent mixture of equal parts of acetone, ethanol, isopropanol and demineralized water for 24 hours. After the solvent mixture has been removed, the hair tresses are washed thoroughly with demineralized water. Subsequently, each hair tress is washed with 3 mL of an ammonium laurylsulfate solution (25% strength), STEPANOL(R) ALS 25, from STEPAN Company, and rinsed with demineralized water until no foam is visible any longer (at least 2 minutes). After the main washing, the tresses are conditioned at 23° C. and 60% air humidity for at least 12 hours prior to further use.

Measurement of combing force: The combing force in wet and dry hair is determined using hair tresses of damaged Caucasian hair from Kerling International Haarfabrik GmbH (hair tresses of damage level B, pulled twice) having a weight of 2 g and a length of 20 cm. The combing force was measured by the double comb method according to Y. K. Kamath and Hans-Dietrich Weigmann, J. Soc. Cosmet. Chem., 37, 111-124, 1986 with an Instron 3343 tensile compression tester. First of all, the wet and dry combing force is determined across the measurement zone from untreated hair tresses. Subsequently, the hair tresses are treated with a cosmetic composition of the invention and the force absorbed in the combing operation is determined. The measurement reported is the reduction in the combing force across the measurement zone (work) that arises between the treated and untreated hair tresses. The average is formed from three hair tresses. The reduction in combing force is reported in percent.

Suppleness:

The measurement principle for determination of the hydrophobicity of hair follows the details given in DE 10 2010 020 192. The softness of the hair was determined using hair tresses of damaged Caucasian hair from Kerling International Haarfabrik GmbH (hair tresses of damage level B, pulled twice) having a weight of 2 g and a length of 20 cm. The hair softness in the dry state was measured by using an Instron 3343 tensile compression tester, by correlating the tensile force required with the parameters of flexural stiffness and surface roughness of the bundle of hair. These two parameters in turn correlate to the hair softness. For this purpose, an untreated hair tress was clamped in a measurement arrangement consisting of five rods opposite and offset from one another. The form of the hair tress in this starting position is a kind of double-S. After this preparation, the hair tress is pulled in one direction out of the measurement arrangement and the necessary force across the measurement zone is evaluated as work. Subsequently, the hair tresses are treated with a cosmetic composition of the invention and the force absorbed in the pulling of the hair tress through the measurement arrangement across the measurement zone is determined. The measurement reported is the reduction in the tensile force across the measurement zone (work) that arises between the treated and untreated hair tresses. A high reduction in tensile force (work) corresponds to good softness or high suppleness. The average is formed from three hair tresses.

Washing procedure for shampoo:

0.1 g of shampoo per g of hair is applied to a cleaned, moistened hair tress. The shampoo is massaged in in the direction of the tips of the hair for 30 seconds. Subsequently, the hair tress is rinsed under flowing demineralized water for 30 s and disentangled with a coarse-toothed comb. The procedure is repeated twice. In the last instance, the rinsing process is extended to 60 s. Subsequently, the hair tress is dried at an air humidity of 60% and a temperature of 23° C. for at least 12 h.

All figures in parts hereinafter relate to parts by weight.

Example 13A to 13B:

Cosmetic composition: shampoo

The examples which follow represent cosmetic compositions comprising emulsions E1 to E2 from example 4 to example 5. The active content of organopolysiloxane in the cosmetic composition is 0.66%.

TABLE 1

| Cosmetic compositions (shampoo) F1 and F2 | | |
|---|---|---|
| Constituents (INCI name) | Example 13 A Cosmetic composition F1 [pts. by wt.] | Example 13 b Cosmetic composition F2 [pts. by wt.] |
| Aqua (DI Water) | ad 100 | ad 100 |
| Guar Hydroxypropyltrimonium Chloride 1) | 0.2 | 0.2 |

TABLE 1-continued

Cosmetic compositions (shampoo) F1 and F2

| Constituents (INCI name) | Example 13 A Cosmetic composition F1 [pts. by wt.] | Example 13 b Cosmetic composition F2 [pts. by wt.] |
|---|---|---|
| Lauryl Polyglucose, Lauryl Glucoside 2) | 21.4 | 21.4 |
| Glycol Distearate 3) | 1.2 | 1.2 |
| PEG-150 Distearate 4) | 0.2 | 0.2 |
| Citric Acid 5) | 0.2 | 0.2 |
| Cocamidopropyl Betaine 6) | 13.4 | 13.4 |
| Emulsion E1 from example 4 | 3.3 | |
| Emulsion E2 from example 5 | | 3.3 |
| Methylchloroisothiazolinone, Methylisothiazolinone 7) | 0.1 | 0.1 |

1) Guar Hydroxypropyltrimonium Chloride: N-Hance(R) 3000, Hercules Inc.
2) Lauryl Polyglucose, Lauryl Glucoside: Plantacare(R) 1200 UP; BASF SE
3) Glycol Distearate: Genapol(R) PMS, Clariant GmbH
4) PEG-150 Distearate: Eumulgin(R) EO 33, BASF SE
5) Citric Acid: Citric Acid, Sigma
6) Cocamidopropyl Betaine: Amphosol CG, STEPAN Company
7) Methylchloroisothiazolinone, Methylisothiazolinone: Kathon™ CG, Rohm and Haas Company, Inc.

Preparation Instructions:

Guar Hydroxypropyltrimonium Chloride is dispersed in water and the mixture is heated to 75° C. Subsequently, Lauryl Polyglucose, Lauryl Glucoside, Glycol Distearate and PEG-150 Distearate are added. After stirring at 75° C. for five minutes, the solution is cooled down to 35° C. while stirring gradually. On attainment of this target temperature, emulsion E1 (analogous procedure for emulsion E2), citric acid, Cocamidopropyl Betaine and the preservative Methylchloroisothiazolinone, Methylisothiazolinone are added and the mixture is cooled to room temperature.

The comparative composition VF3 used is the cosmetic composition from table 1. Rather than emulsions E1 to E2, 5.0 parts of the emulsion VE2 are incorporated into the formulation.

The viscosities of the cosmetic compositions F1 to F2 and VF3 obtained are determined immediately after production and after 12 days.

As shown by table 2 below, the use of the inventive emulsions E1 and E2 in the cosmetic compositions F1 and F2 leads only to a slight drop in the viscosities of the compositions, if any, over time. By contrast, in the case of comparative composition VF3, in which an amino-functionalized polydimethylsiloxane has been used rather than a carbamato-functionalized polydimethylsiloxane, a more distinct drop in viscosity is apparent. The cosmetic compositions F1 and F2 comprising the emulsions of the invention E1 and E2 thus have higher stability.

TABLE 2

Determination of the viscosity of the cosmetic compositions

| cosmetic composition | Viscosity [mPas] directly after production | Viscosity [mPas] after 12 days | Drop in viscosity [mPas] |
|---|---|---|---|
| F1 | 1550 | 1540 | −10 |
| F2 | 1680 | 1512 | −168 |
| VF3 | 2771 | 2280 | −491 |

Example 14

Cosmetic Composition: Shampoo

The example which follows represents a cosmetic composition F4 comprising emulsion E2 from example 5. The active content of organopolysiloxane in the cosmetic composition is 2%.

TABLE 3

Cosmetic composition (shampoo) F4

| Constituents (INCI name) | Cosmetic composition (shampoo) F4 [pts. by wt.] |
|---|---|
| Aqua (DI Water) | Ad 100 |
| Guar Hydroxypropyltrimonium Chloride 1) | 0.2 |
| Sodium Laureth Sulfate 2) | 37.74 |
| Cocamide MIPA 3) | 0.5 |
| Glycol distearate 4) | 1.40 |
| PEG-150 distearate 5) | 0.20 |
| Cocamidopropyl Betaine 6) | 10.07 |
| Emulsion E2 from example 5 | 10 |
| Methylchloroisothiazolinone, Methylisothiazolinone 7) | 0.06 |
| Sodium chloride | 0.15 |

1) Guar Hydroxypropyltrimonium Chloride: N-Hance ® 3000, Hercules Inc.
2) Sodium Laureth Sulfate: Genapol ® LRO 26.5%, Clariant
3) Cocamide MIPA: NINOL M-10, STEPAN Company
4) Glycol Distearate: Genapol ® PMS, Clariant GmbH
5) PEG-150 Distearate: Eumulgin ® EO 33, BASF SE
6) Cocamidopropyl Betaine: Amphosol CG, STEPAN Company
7) Methylchloroisothiazolinone, Methylisothiazolinone: Kathon™ CG, Rohm and Haas Company, Inc.

Preparation Instructions:

Guar Hydroxypropyltrimonium Chloride is dispersed in water and the mixture is heated to 75° C. Subsequently, Sodium Laureth Sulfate, Cocamide MIPA, Glycol distearate and PEG-150 Distearate are added. After stirring at 75° C. for five minutes, the solution is cooled down to 35° C. while stirring gently. On attainment of this target temperature, emulsion E2, Cocamidopropyl Betaine and the preservative Methylchloroisothiazolinone, Methylisothiazolinone are added and the mixture is cooled to room temperature. Finally, sodium chloride is added while stirring.

Comparative Example

The cosmetic composition from table 3 without emulsion E2 is used as comparative composition VF5, i.e. the silicone-free shampoo base.

Table 4 contains the results of the measurement for the parameters of dry combing force, wet combing force and suppleness on hair treated with the inventive cosmetic composition F4 and with the noninventive cosmetic composition VF5 compared to untreated hair.

TABLE 4

Measurement of dry combing force, wet combing force and suppleness

| Cosmetic composition | Reduction in dry combing force (work) compared to untreated hair in % | Reduction in wet combing force (work) compared to untreated hair in % | Increase in suppleness (work) compared to untreated hair in % |
|---|---|---|---|
| F4 | 65 | 60 | 27 |
| VF5 | 33 | 32 | −3 |

Table 4 shows that the use of the inventive emulsion E2 in the cosmetic compositions F4 leads to a distinct improvement in the care properties. The use of the inventive emulsions E2 brings about a reduction in the combing forces to be expended in dry and wet hair. The reduction in the dry and wet combing force in the case of treatment with the inventive composition F4 is much greater compared to the treatment with the noninventive composition VF5. In addition, the suppleness of the hair in the treatment with the inventive composition F4 is improved compared to a treatment with the noninventive cosmetic composition VF5 which does not contain any emulsion of the invention.

Examples 15A and 15B

Cosmetic Composition: Transparent Shampoos

The examples which follow represent cosmetic compositions comprising emulsion E1 from example 4 and emulsion E2 from example 5. The active content of organopolysiloxane in the cosmetic composition is 0.5%.

TABLE 5

Cosmetic compositions (transparent shampoos) F6 and F7

| Constituents (INCI name) | Example 15A cosmetic composition F6 [pts. by wt.] | Example 15B cosmetic composition F7 [pts. by wt.] |
|---|---|---|
| Aqua (DI Water) | Ad 100 | Ad 100 |
| Polyquaternium-10 1) | 0.10 | 0.10 |
| Cocamide MEA | 1.00 | 1.00 |
| Sodium Laureth Sulfate 3) | 52.80 | 52.80 |
| Cocamidopropyl Betaine 4) | 10.06 | 10.06 |
| Methylchloroisothiazolinone, Methylisothiazolinone 5) | 0.06 | 0.06 |
| Emulsion E1 from example 4 | 2.50 | |
| Emulsion E2 from example 5 | | 2.50 |
| Aqua (DI Water) | 15.00 | 15.00 |
| Sodium Chloride | 1.00 | 1.00 |

1) Polyquaternium-10: Ucare™ Polymer JR-400, Amerchol Corporation
2) Cocamide MEA: COMPERLAN ® 100, Cognis Coorporation
3) Sodium Laureth Sulfate: Genapol ® LRO 26.5%, Clariant
4) Cocamidopropyl Betaine: Amphosol CG, STEPAN Company
5) Methylchloroisothiazolinone, Methylisothiazolinone: Kathon ™ CG, Rohm and Haas Company, Inc.

Preparation Instructions:

Polyquaternium-10 is dispersed in water and the mixture is heated to 70° C. while stirring. Subsequently, Sodium Laureth Sulfate and Cocamide MEA are added. After the mixture has been cooled down to 35° C. while stirring gently Cocamidopropylbetaine and the preservatives Methylchloroisothiazolinone, Methylisothiazolinone are added. Subsequently, the water-prediluted emulsion E1 or emulsion E2 is added. By addition of sodium chloride, the viscosity of the shampoo is adjusted to the target region of about 10 000 mPas.

After treatment of damaged Caucasian hair with shampoos F6 and F7 from examples 15A and 15B, this feels softer than untreated hair.

Examples 16A-16G:

Cosmetic composition: rinse-off conditioner 16A-16G

The example which follows represents cosmetic compositions F8 -F14 according to table 6 comprising emulsions E1-E7 from examples 4 to 10. The active content of organopolysiloxane in the cosmetic composition is 0.5% to 2%.

TABLE 6

Cosmetic composition: rinse-off conditioner F8-F14

| Constituents (INCI name) | Ex. 16A cosmet. formul. F8 [pts. by wt.] | Ex. 16B cosmet. formul. F9 [pts. by wt.] | Ex. 16C cosmet. formul. F10 [pts. by wt.] | Ex. 16D cosmet. formul. F11 [pts. by wt.] | Ex. 16E cosmet. formul. F12 [pts. by wt.] | Ex. 16F cosmet. formul. F13 [pts. by wt.] | Ex. 16G cosmet. formul. F14 [pts. by wt.] |
|---|---|---|---|---|---|---|---|
| Water | ad 100 | ad 100 | ad 100 | ad 100 | ad 100 | ad 100 | ad 100 |
| Hydroxyethyl-cellulose 1) | 1.2 | 1.2 | 1.2 | 1.2 | 1.2 | 1.2 | 1.2 |
| Cetyl Alcohol 2) | 1.0 | 1.0 | 1.0 | 1.0 | 1.0 | 1.0 | 1.0 |
| Polysorbate 80 3) | 1.0 | 1.0 | 1.0 | 1.0 | 1.0 | 1.0 | 1.0 |
| Behentrimonium Chloride 4) | 1.8 | 1.8 | 1.8 | 1.8 | 1.8 | 1.8 | 1.8 |
| Stearamidopropyl Dimethylamine 5) | 0.5 | 0.5 | 0.5 | 0.5 | 0.5 | 0.5 | 0.5 |
| Stearyl Alcohol 6) | 3.0 | 3.0 | 3.0 | 3.0 | 3.0 | 3.0 | 3.0 |
| Citric Acid 7) | 0.2 | 0.2 | 0.2 | 0.2 | 0.2 | 0.2 | 0.2 |
| Tetrasodium EDTA 8) | 0.2 | 0.2 | 0.2 | 0.2 | 0.2 | 0.2 | 0.2 |
| Emulsion E1 from ex. 4 | 10.0 | | | | | | |
| Emulsion E2 from ex. 5 | | 5.0 | | | | | |
| Emulsion E3 from ex. 6 | | | 7.5 | | | | |
| Emulsion E4 from ex. 7 | | | | 10.0 | | | |
| Emulsion E5 from ex. 8 | | | | | 2.5 | | |
| Emulsion E6 from ex. 9 | | | | | | 5.0 | |

TABLE 6-continued

Cosmetic composition: rinse-off conditioner F8-F14

| Constituents (INCI name) | Ex. 16A cosmet. formul. F8 [pts. by wt.] | Ex. 16B cosmet. formul. F9 [pts. by wt.] | Ex. 16C cosmet. formul. F10 [pts. by wt.] | Ex. 16D cosmet. formul. F11 [pts. by wt.] | Ex. 16E cosmet. formul. F12 [pts. by wt.] | Ex. 16F cosmet. formul. F13 [pts. by wt.] | Ex. 16G cosmet. formul. F14 [pts. by wt.] |
|---|---|---|---|---|---|---|---|
| Emulsion E7 from ex. 10 | | | | | | | 5.0 |
| Phenoxyethanol, ethylhexylglycerin [9] | 0.9 | 0.9 | 0.9 | 0.9 | 0.9 | 0.9 | 0.9 |

The raw materials named in table 6 are available under the following trade names:
[1] Hydroxyethylcellulose: Tylose ® H 4000 P2, Shin-Etsu Chem. Co.
[2] Cetyl alcohol: Cetyl alcohol, Merck KGaA
[3] Polysorbate 80: Tween™ 80, Croda GmbH
[4] Behentrimonium Chloride: Genamin ® KDMP, Clariant GmbH
[5] Stearamidopropyl Dimethylamine, Incromine™ SB , Croda GmbH
[6] Stearyl alcohol: Stearyl alcohol Merck KGaA
[7] Citric Acid: Citric Acid, Sigma
[8] Tetrasodium EDTA: EDETA ® B powder, BASF Corporation
[9] Phenoxyethanol, ethylhexylglycerin: Euxyl PE 9010, Schülke & Mayr Preparation Instructions:

Water is initially charged and heated to 75° C. while stirring. In the course of this, 1.2 parts hydroxyethyl cellulose are added. Once 65° C. has been attained, 0.5 part Stearamidopropyl Dimethylamine, 1 part Polysorbate 80, 3 parts Stearyl Alcohol, 1 part Cetyl Alcohol and 1.8 parts Behentrimonium Chloride are added. The mixture is stirred until 75° C. has been attained and the ingredients are in dissolved form. Then the mixture is cooled down. During the cooling, 0.2 part Citric Acid and 0.2 part Tetrasodium EDTA are added. At 35° C., 0.9 part Phenoxyethanol, ethylhexylglycerin is added. While continuing to stir, the emulsion from the examples is added. The composition is homogenized while stirring for 15 minutes.

After treatment of damaged Caucasian hair with the rinse-off conditioners F8 to F14 from examples 16A to 16G, this feels softer than untreated hair.

The invention claimed is:

1. An aqueous emulsion, comprising:
(A) at least one carbamato-functionalized organopolysiloxane containing on average per molecule at least one carbamato-functional Y group of the formula $$-R^4-[NX-R^5-]_nNX-H$$

where
X is the same or different and is a hydrogen atom or is a Z radical of the formula $$-CO-O-CHR^6-CH_2-OH \text{ or } -CO-O-CH_2-CHR^6-OH$$

where an average of at least one X radical per molecule is a Z radical,
where $R^4$ is the same or different and is a divalent, Si-C-bonded hydrocarbyl radical having 1 to 18 carbon atoms,
$R^5$ is the same or different and is a divalent hydrocarbyl radical having 1 to 6 carbon atoms,
$R^6$ is the same or different and is a hydrogen atom or a monovalent hydrocarbyl radical having 1 to 36 carbon atoms, and
n is 1, 2, 3 or 4,
with the proviso that, in the carbamato-functionalized organopolysiloxane (A), less than 50 mol % of the N-bonded X radicals in the Y groups are not a hydrogen atom, but have the above meaning of the Z radical, and the carbamato-functionalized organopolysiloxane contains at most 0.7 wt. % of hydroxyl groups, (B) at least one nonionic, polyethylene oxide-containing emulsifier comprising more than 40 ethylene oxide units of the formula —CH$_2$—CH$_2$—O—, and having an HLB value of not less than 15, selected from the group consisting of alkyl polyglycol ethers,
carboxylic acid polyglycol esters,
ethoxylated sorbitan fatty acid esters,
ethoxylated castor oil or hydrogenated variants, ethoxylated fatty amines,
ethoxylated glyceryl fatty acid carboxylates,
block copolymers of ethylene oxide and propylene oxide units that are referred to as poloxamers, and
copolymers of ethylene oxide and propylene oxide units bridged via an ethylenediamine core, and
(C) water,
where the emulsions have particle sizes of not more than 100 nm (D50).

2. The aqueous emulsion of claim 1, wherein the carbamato-functionalized organopolysiloxane(s)(A) are carbamato-functionalized polydiorganosiloxanes of the formula $$[R^1{}_2R^2SiO_{1/2}]_2[R^2(Y)SiO_{2/2}]_k[R^1{}_2SiO_{2/2}]_m \qquad (I)$$

where
$R^1$ is the same or different and is a monovalent Si-C-bonded hydrocarbyl radical having 1 to 18 carbon atoms,
$R^2$ is the same or different and is an $R^1$ radical or a hydroxyl group —OH or alkoxy group of
the formula —O—$R^3$ where $R^3$ is an optionally substituted alkyl radical having 1-8 carbon atoms,
Y is as defined in claim 1,
where an average of at least one Y group per molecule is a Z radical of the formula $$-CO-O-CHR^6-CH_2-OH \text{ or } -CO-O-CH_2-CHR^6-OH$$

where $R^6$ is as defined in claim 1,
m is an integer and is at least 40 and at most 1000,
k is an integer and is at least 1 and at most 15,
where the ratio of m to k is at least 65 and at most 1000.

3. The aqueous emulsion of claim 1, wherein $R^6$ is a methyl radical.

4. The aqueous emulsion of claim 1, wherein in the carbamato-functionalized organopolysiloxane(s)(A), at least 5 mol % of the N-bonded X radicals in the Y groups are not a hydrogen atom, but are Z radicals of the formula $$-CO-O-CHR^6-CH_2-OH \text{ or } -CO-O-CH_2-CHR^6-OH.$$

5. The aqueous emulsion of claim 1, wherein the carbamato-functionalized organopolysiloxanes (A) have at most 0.32% by weight of hydroxyl groups.

6. The aqueous emulsion of claim 1, wherein the carbamato-functionalized organopolysiloxanes (A) have at most 0.17% by weight of hydroxyl groups.

7. The aqueous emulsion of claim 1, wherein the carbamato-functionalized organopolysiloxanes (A) have an amine value of at most 0.3 mmol/g.

8. The aqueous emulsion of claim 1, wherein the carbamato-functionalized organopolysiloxanes (A) have an amine value of at most 0.10 mmol/g.

9. The aqueous emulsion of claim 1, wherein the nonionic, polyethylene oxide-containing emulsifiers (B) which contain more than 40 ethylene oxide units of the formula -CH2-CH2-O- and have an HLB value of not less than 15 are those selected from the group of
alkyl polyglycol ethers,
carboxylic acid polyglycol esters,
ethoxylated castor oil or hydrogenated variants
ethoxylated fatty amines, and
ethoxylated glyceryl fatty acid carboxylates.

10. The aqueous emulsion of claim 1, wherein the carbamato-functionalized organopolysiloxane(s)(A) are prepared by reacting amino-functionalized organopolysiloxane(s)(A') containing on average per molecule at least one group Y' of the formula

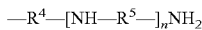

with cyclic carbonates of the formula

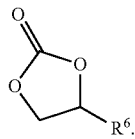

11. The aqueous emulsion of claim 10, wherein the amino-functionalized organopolysiloxane(s)(A') used are amino-functionalized polydiorganosiloxanes (A') of the formula

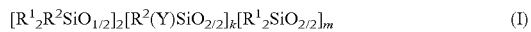 (I)

Where
$R^1$ is the same or different and is a monovalent Si-C-bonded hydrocarbyl radical having 1 to 18 carbon atoms,
$R^2$ is the same or different and is an $R^1$ radical or a hydroxyl group —OH or alkoxy group of the formula —O—$R^3$ where $R^3$ is an optionally substituted alkyl radical having 1-8 carbon atoms,
m is an integer and is at least 40 and at most 1000,
k is an integer and is at least 1 and at most 15,
Y' is as defined in claim 10.

12. The aqueous emulsion of claim 10, wherein the amino-functionalized organopolysiloxane(s) (A') are those having an amine value of at most 0.4 mmol/g.

13. A cosmetic composition comprising,
a cosmetically acceptable medium,
at least one hair conditioner, and
at least one aqueous emulsion of claim 1.

14. The cosmetic composition of claim 13, wherein the hair conditioners are those selected from the group consisting of
cationic polymers,
cationic surfactants,
non-polymeric quaternary ammonium compounds,
organopolysiloxanes and organopolysiloxane copolymers other than the carbamato-functionalized polydiorganosiloxanes (A) present in the aqueous emulsions,
fatty acid esters and fatty acid alcohols,
natural or synthetic oils and waxes,
panthenol, lipids, proteins, hydrolyzed proteins, and mixtures thereof.

15. The cosmetic composition of claim 13, further comprising one or more standard cosmetic additives selected from the group consisting of
surfactants,
thickeners, gelating agents,
film formers,
humectants,
UV filters,
pearlizing agents,
vitamins,
antioxidants,
caffeine,
active antidandruff ingredients,
preservatives
and mixtures thereof.

16. A process for producing a cosmetic composition, comprising mixing at least one aqueous emulsion of carbamato-functionalized organopolysiloxanes of claim 1,
with at least one conditioner,
and optionally with further standard cosmetic additives
in a cosmetically acceptable medium.

17. A process for the treatment of keratinic fibers, comprising applying a cosmetic composition of claim 1 to the keratinic fibers.

18. The aqueous emulsion of claim 2, wherein k is from 1 to 7.

19. The aqueous emulsion of claim 2, wherein the ratio of m to k is at least 130.

* * * * *

UNITED STATES PATENT AND TRADEMARK OFFICE
CERTIFICATE OF CORRECTION

| | | |
|---|---|---|
| PATENT NO. | : 11,197,818 B2 | Page 1 of 1 |
| APPLICATION NO. | : 16/096184 | |
| DATED | : December 14, 2021 | |
| INVENTOR(S) | : Brehm et al. | |

It is certified that error appears in the above-identified patent and that said Letters Patent is hereby corrected as shown below:

In the Claims

Column 30, Lines 23-24, Claim 15:
After "further comprising one or more"
Delete "standard".

Column 30, Line 43, Claim 16:
After "and optionally with further"
Delete "standard".

Signed and Sealed this
Twenty-sixth Day of April, 2022

Katherine Kelly Vidal
*Director of the United States Patent and Trademark Office*